US012758376B2

(12) United States Patent
Jönsson

(10) Patent No.: US 12,758,376 B2
(45) Date of Patent: Oct. 13, 2026

(54) INTRODUCER ASSEMBLY FOR MINIMALLY INVASIVE DEPLOYMENT OF A MEDICAL DEVICE IN A VESSEL

(71) Applicant: Emboline, Inc., Santa Cruz, CA (US)

(72) Inventor: Anders Jönsson, Bromma (SE)

(73) Assignee: Emboline, Inc., Santa Cruz, CA (US)

( * ) Notice: Subject to any disclaimer, the term of this patent is extended or adjusted under 35 U.S.C. 154(b) by 0 days.

(21) Appl. No.: 18/522,032

(22) Filed: Nov. 28, 2023

(65) Prior Publication Data

US 2024/0173116 A1 May 30, 2024

(30) Foreign Application Priority Data

Nov. 28, 2022 (EP) .................................... 22210053

(51) Int. Cl.

| | |
|---|---|
| ***A61F 2/01*** | (2006.01) |
| *A61F 2/24* | (2006.01) |
| *A61M 25/00* | (2006.01) |
| *A61M 25/09* | (2006.01) |

(52) U.S. Cl.

CPC .............. *A61F 2/011* (2020.05); *A61F 2/013* (2013.01); *A61F 2/2427* (2013.01); *A61M 25/0097* (2013.01); *A61M 25/09* (2013.01); *A61M 2025/09125* (2013.01)

(58) Field of Classification Search

CPC ........ A61F 2/011; A61F 2/013; A61F 2/9517; A61F 2/2427; A61M 2025/09116; A61M 25/09; A61M 2025/09125

See application file for complete search history.

(56) References Cited

U.S. PATENT DOCUMENTS

| | | | |
|---|---|---|---|
| 4,850,358 | A | 7/1989 | Millar |
| 5,411,552 | A | 5/1995 | Anderson et al. |
| 5,468,225 | A | 11/1995 | Teirstein |
| 5,584,803 | A | 12/1996 | Stevens et al. |
| 5,667,523 | A | 9/1997 | Bynon et al. |
| 5,678,570 | A | 10/1997 | Manning |
| 5,766,151 | A | 6/1998 | Valley et al. |
| 5,769,812 | A | 6/1998 | Stevens et al. |
| 5,769,816 | A | 6/1998 | Barbut et al. |

(Continued)

FOREIGN PATENT DOCUMENTS

| | | | |
|---|---|---|---|
| EP | 2732794 | A1 | 5/2014 |
| EP | 2859864 | A1 | 4/2015 |

(Continued)

OTHER PUBLICATIONS

European Patent Office, Extended European Report, Opinion and Search Strategy dated Apr. 26, 2023 in European Patent Application No. 22210053.9-1113, 11 pages.

(Continued)

*Primary Examiner* — Katherine M Shi
(74) *Attorney, Agent, or Firm* — Shay Glenn LLP

(57) ABSTRACT

An introducer assembly is disclosed for minimally invasive deployment of a medical device in a vessel including a handle, comprising a locking mechanism for locking a guidewire relative said handle. The medical device is for example an embolic protection device such as a deflection filter. A position of said guidewire relative said handle can thus be provided to control a position of the deflection filter in the vessel.

14 Claims, 5 Drawing Sheets

(56) References Cited

U.S. PATENT DOCUMENTS

| | | | |
|---|---|---|---|
| 5,795,325 | A | 8/1998 | Valley et al. |
| 5,868,708 | A | 2/1999 | Hart et al. |
| 5,910,154 | A | 6/1999 | Tsugita et al. |
| 5,916,193 | A | 6/1999 | Stevens et al. |
| 5,957,949 | A | 9/1999 | Leonhardt et al. |
| 6,051,014 | A | 4/2000 | Jang |
| 6,117,064 | A | 9/2000 | Apple et al. |
| 6,139,517 | A | 10/2000 | Macoviak et al. |
| 6,142,987 | A | 11/2000 | Tsugita |
| 6,214,026 | B1 * | 4/2001 | Lepak .................... A61F 2/013 604/104 |
| 6,235,044 | B1 | 5/2001 | Root et al. |
| 6,245,088 | B1 | 6/2001 | Lowery |
| 6,258,120 | B1 | 7/2001 | McKenzie et al. |
| 6,290,656 | B1 | 9/2001 | Boyle et al. |
| 6,348,063 | B1 | 2/2002 | Yassour et al. |
| 6,361,545 | B1 | 3/2002 | Macoviak et al. |
| 6,371,935 | B1 | 4/2002 | Macoviak et al. |
| 6,395,014 | B1 | 5/2002 | Macoviak et al. |
| 6,402,736 | B1 | 6/2002 | Brown et al. |
| 6,537,294 | B1 | 3/2003 | Boyle et al. |
| 6,547,760 | B1 | 4/2003 | Samson et al. |
| 6,585,715 | B1 | 7/2003 | Teirstein |
| 6,620,182 | B1 | 9/2003 | Khosravi et al. |
| 6,673,089 | B1 | 1/2004 | Yassour et al. |
| 6,689,150 | B1 | 2/2004 | Van Tassel et al. |
| 6,709,415 | B2 | 3/2004 | Navia et al. |
| 7,323,001 | B2 | 1/2008 | Clubb et al. |
| 7,371,250 | B2 | 5/2008 | Mazzocchi et al. |
| 7,637,920 | B2 | 12/2009 | von Lehe et al. |
| 7,651,514 | B2 | 1/2010 | Salahieh et al. |
| 7,749,245 | B2 | 7/2010 | Cohn et al. |
| 8,221,445 | B2 | 7/2012 | Van Tassel et al. |
| 8,388,644 | B2 | 3/2013 | Parker |
| 8,512,398 | B2 | 8/2013 | Alkhatib |
| 8,778,017 | B2 | 7/2014 | Eliasen et al. |
| 8,840,663 | B2 | 9/2014 | Salahieh et al. |
| 8,974,490 | B2 | 3/2015 | Jonsson |
| 9,023,101 | B2 | 5/2015 | Krahbichler |
| 9,579,182 | B2 | 2/2017 | Krahbichler |
| 9,968,359 | B2 | 5/2018 | Jonsson |
| 10,076,400 | B2 | 9/2018 | Krahbichler |
| 10,433,946 | B2 | 10/2019 | Krahbichler |
| 10,466,946 | B2 | 11/2019 | Watanabe |
| 10,512,468 | B2 | 12/2019 | Jonsson |
| 10,568,736 | B2 | 2/2020 | Meiri et al. |
| 10,575,852 | B2 | 3/2020 | Jonsson |
| 10,610,229 | B2 | 4/2020 | Jonsson |
| 11,278,388 | B2 | 3/2022 | Krahbichler |
| 11,446,132 | B2 | 9/2022 | Krahbichler |
| 11,957,561 | B2 | 4/2024 | Krahbichler |
| 11,992,398 | B2 | 5/2024 | Krahbichler |
| 12,402,997 | B2 | 9/2025 | Krahbichler |
| 2001/0044591 | A1 | 11/2001 | Stevens et al. |
| 2002/0002383 | A1 | 1/2002 | Sepetka et al. |
| 2002/0077596 | A1 | 6/2002 | McKenzie et al. |
| 2002/0095141 | A1 | 7/2002 | Belef et al. |
| 2002/0133115 | A1 | 9/2002 | Gordon et al. |
| 2002/0143362 | A1 | 10/2002 | Macoviak et al. |
| 2002/0161389 | A1 | 10/2002 | Boyle et al. |
| 2002/0169437 | A1 | 11/2002 | Macoviak et al. |
| 2003/0004539 | A1 | 1/2003 | Linder et al. |
| 2003/0040736 | A1 | 2/2003 | Stevens et al. |
| 2003/0078519 | A1 | 4/2003 | Salahleh et al. |
| 2003/0130680 | A1 | 7/2003 | Russell |
| 2003/0153942 | A1 | 8/2003 | Wang et al. |
| 2003/0153943 | A1 | 8/2003 | Michael et al. |
| 2003/0158574 | A1 | 8/2003 | Esch et al. |
| 2003/0171803 | A1 | 9/2003 | Shimon |
| 2003/0195609 | A1 | 10/2003 | Berenstein et al. |
| 2003/0199759 | A1 | 10/2003 | Richard |
| 2004/0073253 | A1 | 4/2004 | Morrill et al. |
| 2004/0215167 | A1 | 10/2004 | Belson |
| 2004/0225354 | A1 | 11/2004 | Allen et al. |
| 2005/0055047 | A1 | 3/2005 | Greenhalgh |
| 2005/0085842 | A1 | 4/2005 | Eversull et al. |
| 2005/0119688 | A1 | 6/2005 | Bergheim |
| 2005/0137689 | A1 | 6/2005 | Salahieh et al. |
| 2005/0137696 | A1 | 6/2005 | Salahleh et al. |
| 2005/0209582 | A1 | 9/2005 | Quinn et al. |
| 2005/0216031 | A1 | 9/2005 | White et al. |
| 2006/0015138 | A1 | 1/2006 | Gertner |
| 2006/0020285 | A1 | 1/2006 | Niermann |
| 2006/0025806 | A1 | 2/2006 | Krolik et al. |
| 2006/0074484 | A1 | 4/2006 | Huber |
| 2006/0074485 | A1 | 4/2006 | Realyvasquez |
| 2006/0161241 | A1 | 7/2006 | Barbut et al. |
| 2006/0241675 | A1 | 10/2006 | Johnson et al. |
| 2006/0253148 | A1 | 11/2006 | Leone et al. |
| 2006/0259066 | A1 | 11/2006 | Euteneuer |
| 2006/0287668 | A1 | 12/2006 | Fawzi et al. |
| 2007/0027534 | A1 | 2/2007 | Bergheim et al. |
| 2007/0088383 | A1 | 4/2007 | Pal et al. |
| 2007/0142906 | A1 | 6/2007 | Figulla et al. |
| 2007/0270901 | A1 | 11/2007 | Shimon et al. |
| 2008/0004688 | A1 | 1/2008 | Spenser et al. |
| 2008/0065145 | A1 | 3/2008 | Carpenter |
| 2008/0140110 | A1 | 6/2008 | Spence |
| 2008/0147111 | A1 | 6/2008 | Johnson et al. |
| 2008/0147160 | A1 | 6/2008 | Ghione et al. |
| 2008/0147181 | A1 | 6/2008 | Ghione et al. |
| 2008/0147182 | A1 | 6/2008 | Righini et al. |
| 2008/0269877 | A1 | 10/2008 | Jenson et al. |
| 2009/0030510 | A1 | 1/2009 | Ho |
| 2009/0062836 | A1 | 3/2009 | Kurrus |
| 2009/0254172 | A1 | 10/2009 | Grewe |
| 2009/0287182 | A1 | 11/2009 | Bishop et al. |
| 2009/0326575 | A1 | 12/2009 | Galdonik et al. |
| 2010/0076482 | A1 | 3/2010 | Shu et al. |
| 2010/0094209 | A1 | 4/2010 | Drasler et al. |
| 2010/0099946 | A1 | 4/2010 | Jenkins et al. |
| 2010/0179583 | A1 | 7/2010 | Carpenter et al. |
| 2010/0179584 | A1 | 7/2010 | Carpenter et al. |
| 2010/0191276 | A1 | 7/2010 | Lashinski |
| 2010/0211095 | A1 | 8/2010 | Carpenter |
| 2010/0228280 | A1 | 9/2010 | Groothuis et al. |
| 2010/0312268 | A1 | 12/2010 | Belson |
| 2010/0324589 | A1 | 12/2010 | Carpenter et al. |
| 2011/0040232 | A1 | 2/2011 | Magal |
| 2011/0172697 | A1 | 7/2011 | Jonsson |
| 2011/0270388 | A9 | 11/2011 | Stevens |
| 2012/0172915 | A1 | 7/2012 | Fifer et al. |
| 2013/0103075 | A1 | 4/2013 | Wang et al. |
| 2013/0123835 | A1 | 5/2013 | Anderson et al. |
| 2013/0184739 | A1 | 7/2013 | Brady et al. |
| 2013/0238010 | A1 | 9/2013 | Johnson et al. |
| 2013/0245669 | A1 | 9/2013 | Basu et al. |
| 2014/0074148 | A1 | 3/2014 | Glenn et al. |
| 2014/0074152 | A1 | 3/2014 | Shezifi et al. |
| 2014/0243878 | A1 | 8/2014 | Urbanski et al. |
| 2014/0257362 | A1 | 9/2014 | Eidenschink |
| 2015/0066075 | A1 | 3/2015 | Russell et al. |
| 2016/0324621 | A1 | 11/2016 | Shezifil et al. |
| 2017/0181835 | A1 | 6/2017 | Kleshinski et al. |
| 2020/0121356 | A1 * | 4/2020 | Look .............. A61B 17/320758 |
| 2020/0197016 | A1 | 6/2020 | Jonsson |
| 2022/0387162 | A1 | 12/2022 | Krahbichler |
| 2023/0091397 | A1 | 3/2023 | Kleshinski et al. |
| 2024/0245500 | A1 | 7/2024 | Krahbichler |
| 2024/0307167 | A1 | 9/2024 | Krahbichler |

FOREIGN PATENT DOCUMENTS

| | | | |
|---|---|---|---|
| JP | 2003517592 | A | 5/2003 |
| JP | 2011525405 | A | 9/2011 |
| WO | WO97/42878 | A1 | 11/1997 |
| WO | WO99/12478 | A1 | 3/1999 |
| WO | WO99/32050 | A1 | 7/1999 |
| WO | WO00/43062 | A1 | 7/2000 |
| WO | WO00/44313 | A1 | 8/2000 |
| WO | WO01/08743 | A1 | 2/2001 |
| WO | WO01/35870 | A1 | 5/2001 |
| WO | WO01/56484 | A1 | 8/2001 |
| WO | WO02/056955 | A1 | 7/2002 |

(56) References Cited

FOREIGN PATENT DOCUMENTS

| | | | |
|---|---|---|---|
| WO | WO2006/029370 | A2 | 3/2003 |
| WO | WO03/047648 | A2 | 6/2003 |
| WO | WO03/105721 | A2 | 12/2003 |
| WO | WO2004/006803 | A1 | 1/2004 |
| WO | WO2004/006804 | A1 | 1/2004 |
| WO | WO2004/019817 | A1 | 3/2004 |
| WO | WO2004/021922 | A2 | 3/2004 |
| WO | WO2004/043293 | A2 | 5/2004 |
| WO | WO2005/023358 | A1 | 3/2005 |
| WO | WO2007/035885 | A2 | 3/2007 |
| WO | WO2007/149107 | A1 | 12/2007 |
| WO | WO2008/033845 | A2 | 3/2008 |
| WO | WO2009/049677 | A1 | 4/2009 |
| WO | WO2011/132080 | A2 | 10/2011 |
| WO | WO2012/009558 | A2 | 1/2012 |
| WO | WO2012/085916 | A2 | 6/2012 |
| WO | WO2012/094195 | A1 | 7/2012 |
| WO | WO2012/171720 | A1 | 12/2012 |
| WO | WO2013/063124 | A1 | 5/2013 |
| WO | WO2013/142386 | A1 | 9/2013 |
| WO | WO2018/206160 | A1 | 11/2018 |
| WO | WO2019/081689 | A1 | 5/2019 |

OTHER PUBLICATIONS

Reichenspurner et al.; Particulate emboli capture by an intra-aortic filter device during cardiac surgery; The Journal of Thoracic and Cardiovascular Surgery; 119(2); pp. 233-241; Feb. 1, 2000.
Reimers et al.; Cerebral protection with filter devices during carotid artery stenting; Circulation; 104(1); pp. 12-15; Jul. 3, 2001.
Krahbichler; U.S. Appl. No. 19/290,337 entitled "Embolic protection device and method," filed Aug. 4, 2025.

* cited by examiner

INTRODUCER ASSEMBLY FOR MINIMALLY INVASIVE DEPLOYMENT OF A MEDICAL DEVICE IN A VESSEL

RELATED APPLICATIONS

This application claims priority under 35 U.S.C. § 119 to European application No. 22210053.9 filed Nov. 28, 2022 entitled An Introducer Assembly For Minimally Invasive Deployment Of A Medical Device In A Vessel, which is hereby incorporated herein by reference in its entirety.

TECHNICAL FIELD

This disclosure pertains in general to introducer assemblies for minimally invasive deployment of a medical device in a vessel, e.g. cerebral embolic protection assemblies to prevent emboli from entering arteries branching from the aorta, e.g., arteries that lead to the brain. In particular, the disclosure relates to improvements of cerebral embolic protection assemblies.

BACKGROUND

Particles such as emboli may form, for example, as a result of the presence of particulate matter in the bloodstream. Particulate matter may originate from for example a blood clot occurring in the heart. The particulate may be a foreign body, but may also be derived from body tissues. For example, atherosclerosis, or hardening of the blood vessels from fatty and calcified deposits, may cause particulate emboli to form. Moreover, clots can form on the luminal surface of the atheroma, as platelets, fibrin, red blood cells and activated clotting factors may adhere to the surface of blood vessels to form a clot.

Various medical procedures may perturb blood vessels or surrounding tissues. When this occurs, potentially harmful particulates, such as emboli, may be released into the blood stream. These particulates can be damaging, e.g., if they restrict blood flow to the brain. Since emboli are typically particulate in nature, various types of filters have been proposed in an attempt to remove or divert such particles from the bloodstream before they can cause damage to bodily tissues. As intravascular devices and procedures, such as Transcatheter Aortic Valve Implantation (TAVI), become more advanced, there is an emerging need for features that provide these devices with improved ease of use, intravascular stability, and embolic protection. Devices to block or divert particulates from flowing into particular regions of the vasculature have been proposed but may not eliminate the risks associated with the release of potentially harmful particulates into the blood stream during or after particular medical procedures.

Possible areas of improvements of such devices and procedures include prevention of "windsailing" of devices with pulsatile blood flow, leakage of fluid and/or particulate matter at peripheral portions of devices during use thereof, secure positioning in a patient during use and/or retrievability, etc.

Hence, an improved intravascular device, system and/or method would be advantageous and in particular allowing for increased flexibility, cost-effectiveness, and/or patient safety would be advantageous.

An object of the invention is to define a cerebral embolic protection assembly that further increases patient safety.

SUMMARY

Accordingly, embodiments of the present invention preferably seek to mitigate, alleviate or eliminate one or more deficiencies, disadvantages or issues in the art, such as the above-identified, singly or in any combination by providing devices, assemblies, kits, systems and methods according to the appended patent claims. The present invention is defined by the appended claims only, in particular by the scope of appended independent claim(s). Reference(s) to "embodiments" throughout the description which are not under the scope of the appended claims merely represents possible exemplary executions and are therefore not part of the present invention.

The aforementioned objects are achieved according to the disclosure.

In a broad aspect of the disclosure, an introducer assembly is provided for minimally invasive deployment of a medical device in a vessel. The assembly generally includes a handle, and a locking mechanism for locking a guidewire relative said handle.

In an aspect of the disclosure, an embolic protection assembly is provided comprising an embolic protection device, a hypotube running through a catheter or sheath and a handle. The embolic protection assembly further comprises a locking mechanism that is configured to be able to positionally lock a guidewire in relation to for example either the hypotube, the sheath, the catheter or the handle. In some embodiments the handle comprises the locking mechanism. In further embodiments the locking mechanism of the embolic protection assembly may comprise a dampening function.

In one aspect of the disclosure, a cerebral embolic protection assembly is provided comprising an embolic protection device comprising a filter unit, a sheath or catheter, and a tube directly or indirectly attached to the embolic protection device. The sheath or catheter may for example be a part of a delivery system, the tube may for example be a hypotube. During use a guidewire is drawn through the tube and the tube is drawn through the sheath or catheter. The assembly further comprises a locking mechanism comprising a lockable passage. The lockable passage may be structured in many different ways, a first example is using a screw that can squeeze/lock a guidewire within the lockable passage when turned in a first direction and create an open passage in the lockable passage when turned in a second direction. Another example is to have a lever that can be flipped between two positions, where in a first position of the lever a guidewire is squeezed/locked within the lockable passage and in a second position of the lever leaves an open passage in the lockable passage. The locking mechanism is arranged in the assembly such that during use a guidewire drawn through the tube is also drawn through the lockable passage. During use the locking mechanism in a first state is configured to positionally lock a guidewire that is going through the lockable passage, positionally locked in relation to the lockable passage. The locking mechanism in a second state is configured to let a guidewire move freely through the lockable passage, suitably by an open passage through the lockable passage.

In some embodiments the locking mechanism is further configured in the first state to subject a guidewire through it in use to a predetermined friction so that for as long as a guidewire is subjected to a force in relation to the locking mechanism that is below a first predetermined force level, it is positionally locked. When a guidewire is subjected to a force in relation to the locking mechanism that is above the first predetermined force level, then the predetermined friction is overcome, and a guidewire can thus slide through the lockable passage.

In some embodiments the locking mechanism is further configured in the first state to change to the second state if a guidewire through it in use is subjected to a force in relation to the locking mechanism that is above a second predetermined force level.

In some embodiments the locking mechanism may further comprise a dampening function. Then advantageously, when the locking mechanism is in the first state, the dampening function is configured when in use to enable to displace the lockable passage in relation to a first end of the locking mechanism. The displacement is preferable up to a predetermined maximum length when a guidewire that is positionally locked in the lockable passage is subjected to at least a third predetermined force level. It is often suitable that the third predetermined force level is a function of the displacement of the lockable passage. Preferably the dampening function comprises one or more springs and/or one or more spring mechanisms. The one or more springs and/or one or more spring mechanisms can suitably be either linear, progressive, or a mix of both. The dampening function may be symmetrical or asymmetrical in relation to the lockable passage.

In some embodiments the embolic protection assembly further comprises a handle. Then the locking mechanism may positionally lock a guidewire in relation to the handle.

The different additional enhancements of the embolic protection assembly according to the invention can be combined in any desired manner as long as no conflicting features are combined.

The aforementioned object is also achieved by an embolic protection assembly comprising an embolic protection device, a tube such as a hypotube running through a catheter or sheath, and possibly a handle. The embolic protection assembly further comprises a locking mechanism that is configured to, in use, be able to positionally lock a guidewire in relation to for example either the sheath, the catheter, or the handle. In some embodiments the handle comprises the locking mechanism. In further embodiments the locking mechanism of the embolic protection assembly comprises a dampening function.

A primary purpose is to provide a means to be able to perform an operation with improved safety when using a cerebral embolic protection assembly. This is obtained by having a locking mechanism positionally locking a guidewire, thus avoiding to manually hold the guidewire. Other advantages will become apparent from the detailed description.

BRIEF DESCRIPTION OF THE DRAWINGS

Some examples will now be described in more detail for explanatory, and in no sense limiting, purposes, with reference to the following figures, in which.

DETAILED DESCRIPTION

Figure 1:
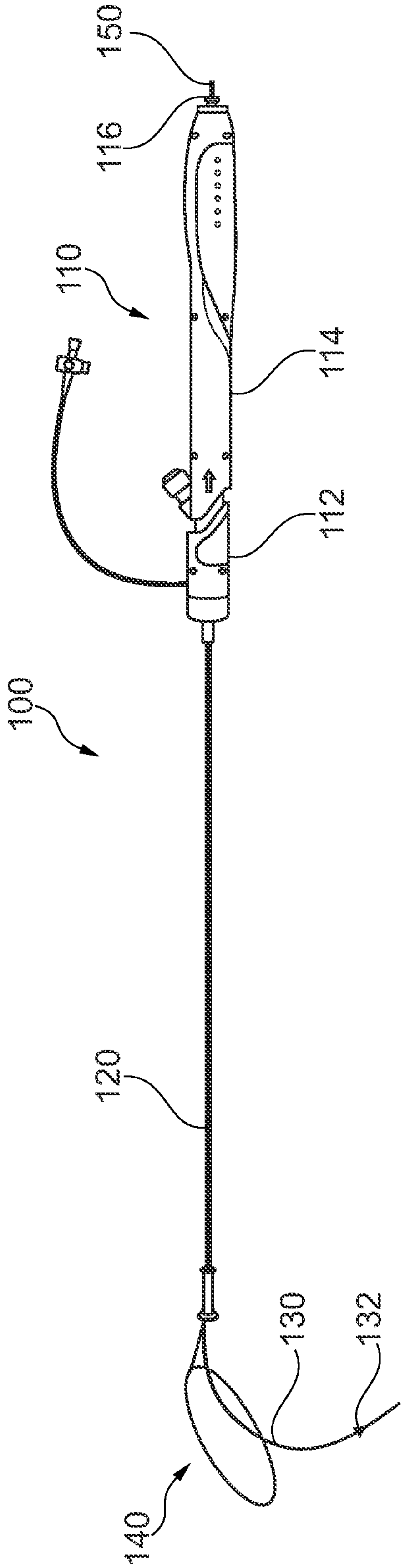
FIG. 1 illustrates an embolic protection assembly 100 laid out flat in a deployed state.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

In order to clarify the assembly according to some examples and of their use will now be described in connection with FIGS. 1 to 5.

The present disclosure focuses on examples of the present invention defining an improved introducer assembly, such as an embolic protection assembly for example comprising an embolic protection device with a deflection-filter. The embolic protection device, suitably a collapsible embolic protection device, is in examples configured for delivery to an aortic arch of a patient and keeping it there in place for protection of side branch vessels of the aortic arch from embolic material. In particular, an embolic protection device having a deflection-filter membrane with a two- or three-dimensional structure. The embolic protection device is preferably delivered transvascularly, for instance in a transfemoral approach. In some alternative examples, the device may be configured to be delivered through side branch vessels of the aortic arch.

Examples of embolic protection devices are disclosed in WO 2019/081689 A1 or WO 2018/206160A1 which are incorporated herein by reference in their entirety for all purposes.

FIG. 1 illustrates an example of an embolic protection assembly 100 laid out flat in a deployed state to be able to visualize all the different parts and how they are interconnected. The embolic protection assembly 100 comprises a handle 110 for delivery, deployment and retrieval. The handle 110 in the illustrated example is a two part handle. The handle 110 is shown in the deployed state with the two parts of the handle pushed together, in a deployed state an embolic protection device 140 is pushed out of a delivery system 120. For retrieval, the two parts of the handle 110 are pulled apart, the embolic protection device 140 is pulled into the delivery system 120. A distal part 112 of the handle 110 is connected to the delivery system 120, suitably a sheath or catheter. A proximal part 114 of the handle 110 is connected to a proximal end of a hypotube 130. The hypotube 130 can suitably be a nitinol curved hypotube shaft. The curvature of the hypotube 130 is configured to press the embolic protection device 140 comprising a deflection-filter 142 into place when deployed, and then keeping it in place until it is retrieved.

The deflection-filter 142 membrane is arranged to separate a first fluid volume of the aortic side branch vessels from a second fluid volume in the aortic arch when the protection unit is positioned in the aortic arch and maintained by a hypotube. The deflection-filter 142 membrane may be a 3-dimensional structure, such as a dome-shape. This may create space underneath the embolic protection device 140 and also may provide optimized filtering due to a larger filter area in relation to a flat or near flat deflection-filter 142 membrane.

The embolic protection device 140 can for example suitably comprise a self-positioning nitinol support frame without stabilizers with a PEEK mesh as a deflection-filter 142 or for example a nitinol frame with stabilizers and a nitinol mesh.

The deflection-filter 142 may suitably be made of an elastic and atraumatic material such as a polymer, e.g. a mesh made from a plurality of fibers made of polymer, nylon, nitinol, or metal, or a combination thereof. The mesh may be made from woven fibers. Fibers may be from about 20 to 50 μm in thickness. Alternatively, the deflection-filter 142 may be a perforated film. When a perforated film is present, the pores formed in the perforated film may include pores of varied or unvaried shape (e.g., rectilinear or rhomboid pores), have a varied or constant density across the film, and/or have a constant or varied size. The size of the pores of the filter allows passage of blood cells (e.g., red blood cells (erythrocytes), white blood cells (leukocytes), and/or platelets (thrombocytes)) and plasma, while being impermeable to particles (e.g., emboli) larger than the pore dimensions. Emboli filtered by the mesh of the filter of the present disclosure are typically particles larger in one or more dimensions than an aperture of the mesh of the filter. The deflection-filter 142 is further advantageously configured for collapsibility and/or crimpability of the embolic protection device 140.

The deflection-filter 142 of the embolic protection device is coupled to a distal part of the hypotube 130 via a device-tail/connection-mechanism 144 with a connector 146. The connection-mechanism 144 may in some embodiments have an integrated connector 146 and/or an integrated coupling to the deflection-filter. In other embodiments the connector 146 and/or the coupling to the deflection-filter 140 may be at least partly comprised of separate parts in relation to the connection-mechanism 144. In some embodiments the coupling to the deflection-filter may pivot. The connection-mechanism 144 can for example be a twisted wire suitably made of nitinol for a flexible connection-mechanism 144. Alternatively, the connection-mechanism 144 may be more or less rigid, for example made from a laser cut tube.

At a proximal end of the proximal part of the handle 114, there is a port 116 for a guide wire 150. A proximal part of the guidewire 150 will stick out here during use. A distal end of the hypotube 130 suitably comprises an atraumatic tip 132, from which a distal part of the guidewire 150 appears during use.

During use of this embolic protection assembly 100, after deployment of the embolic protection device there will be one person holding the handle 110 to make sure that the hypotube 130 is pushed up towards the deflection-filter 140 with a suitable force and making sure that it is in the correct place. A further person will ensure that the guidewire 150 is kept in place.

To improve ease of use and relieve one person or at least one hand of one person to hold the guidewire in place, according to the invention a locking mechanism is applied to the guidewire to replace manually holding the guidewire. The locking mechanism should preferably be activated to lock a guidewire first when the embolic protection device is deployed and in place, and unlocked when readjustment is necessary. The locking mechanism movably locks the guidewire in relation to an entry point into the body or in relation to the handle, or in relation to a catheter or sheath in which the guidewire is running.

Figure 2A:
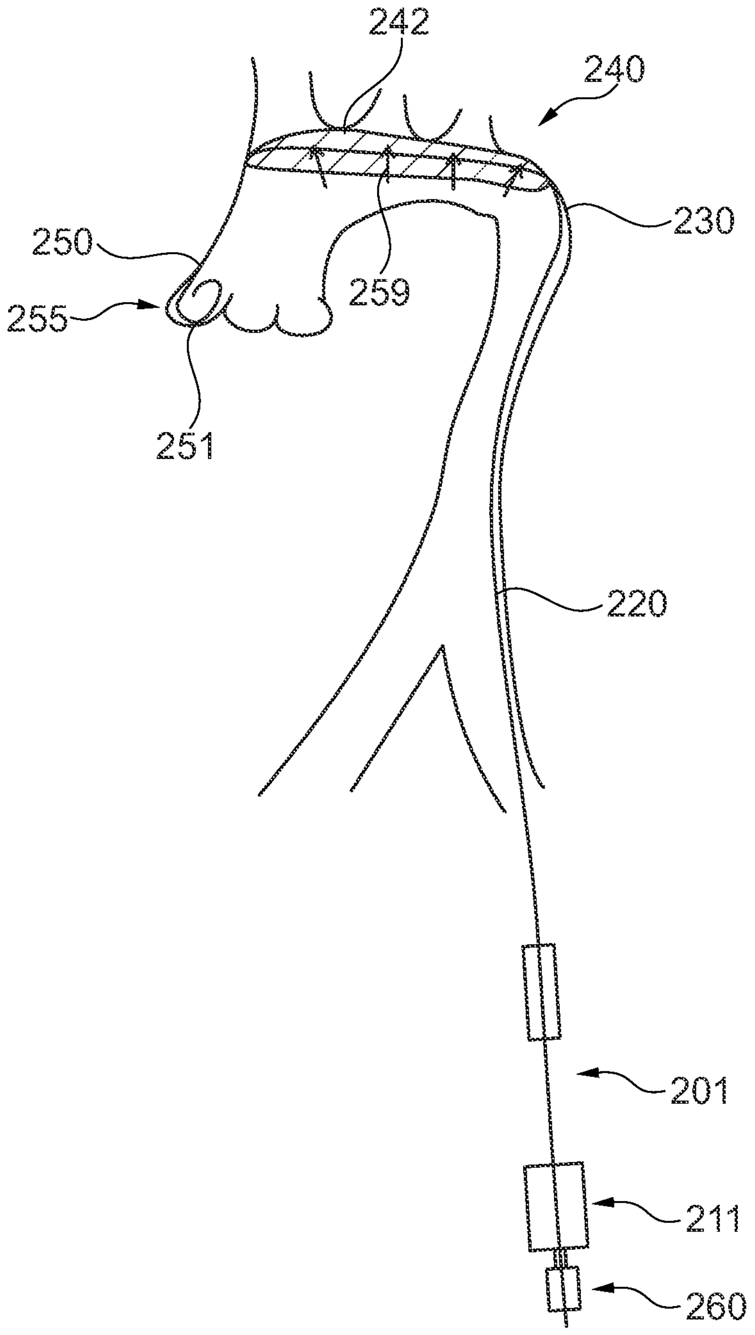
FIG. 2*a*,2*b* illustrate deployed embolic protection assemblies 201 according to the invention in use.

FIG. 2*a* illustrates a simplified deployed embolic protection assembly 201 according to the invention in use. The embolic protection assembly 201 comprises a handle 211, a delivery system 220, a hypotube 230, an embolic protection device 240 comprising a deflection/filter 242, a guidewire 250 with a pigtail distal end 251, and a locking mechanism 260. The guidewire 250 runs through the hypotube 230, which in turn goes underneath the deflection/filter 242 of the embolic protection device 240. The locking mechanism 260 positionally locks the guidewire 250 for example in relation to the handle 211. The distal end 251 of the guidewire rests against a valve 255 which enables the guidewire to be pushed against the valve forcing the hypotube 230 to press up 259 against the deflection/filter 242. Thus, by regulating under what pressure the guidewire 250 is positionally locked, it is possible to regulate the force with which the hypotube is pressing up against the deflection/filter 242.

Figure 2B:
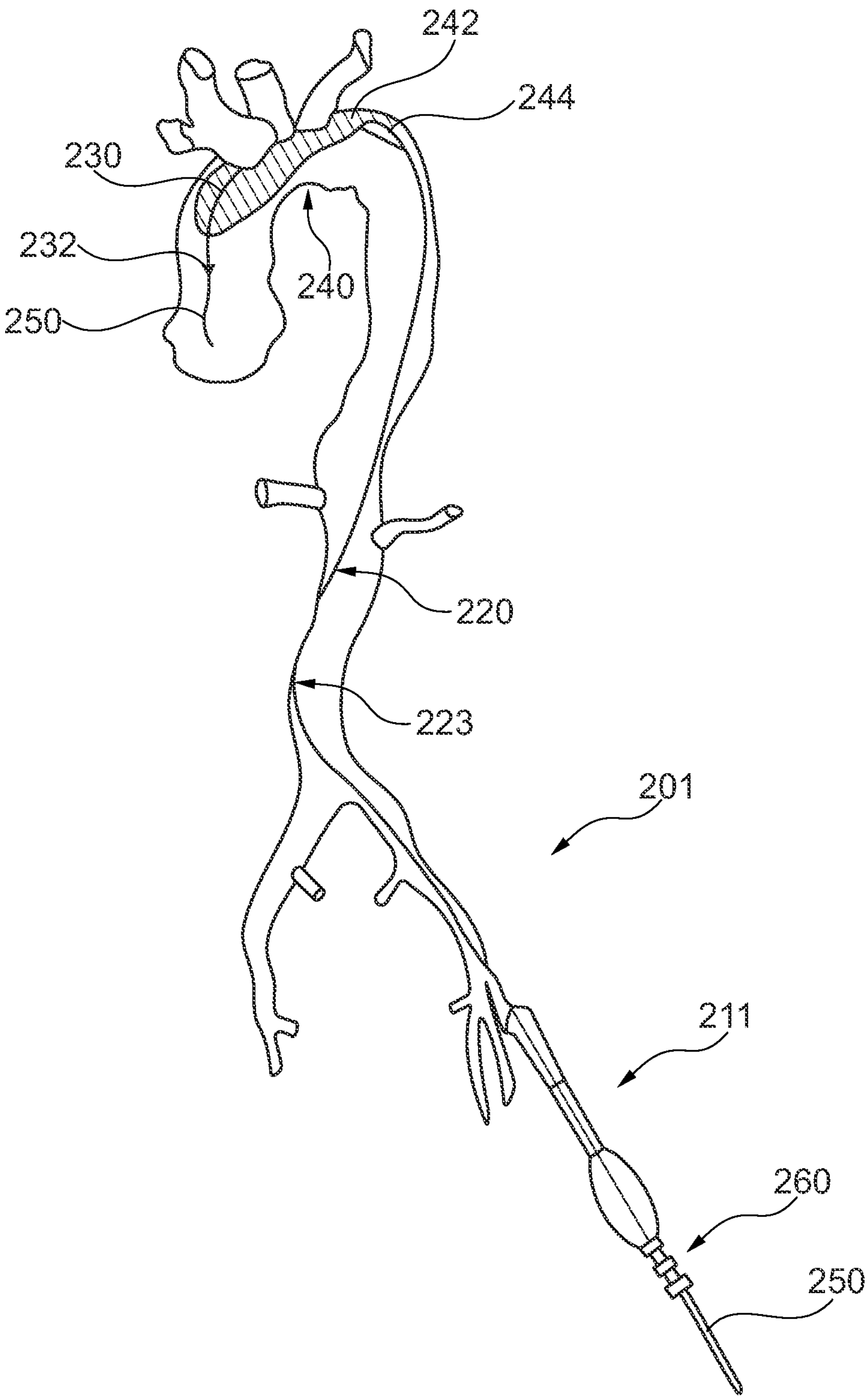

FIG. 2*b* illustrates an in use deployed embolic protection assembly 201 according to the invention. The embolic protection assembly 201 comprises a handle 211, a delivery system 220, a hypotube 230, and an embolic protection device 240. The embolic protection device 240 in turn comprises a deflection filter 242 with a connection-mechanism 244 coupled to a hypotube 230. The hypotube 230 suitably comprises an atraumatic tip 232 at its distal end. An example of a locking mechanism 260 of a guidewire 250 according to the invention is illustrated being attached to the handle or being integrated with the handle at a proximal end of the handle 211. The embolic protection assembly is illustrated in place in the aortic arch and the embolic protection device 240 fully deployed. The embolic protection device is suitably a self-aligning and self-expanding 3-dimensional structure that will line the inner wall of the aortic arch. The embolic protection device suitably spans over the whole apex from the ascending aorta to the descending aorta of the aortic arch preventing emboli from entering any of the side branches, which are supplying blood to the brain. A large filtering area will provide good filtering and provide a better sealing against the walls of the aortic arch. As can be seen in the figure, the delivery system 220 has a forced arch 223 indicating that the handle with a positionally locked guidewire is being pressed towards the aortic arch, resulting in the hypotube 230 being pressed up towards the deflection filter 242, thus keeping the embolic protection device 240 sealed in place during a complete heart cycle.

The locking mechanism 260 can be a part of the handle 211 or be a separately applicable locking mechanism 260 attached to the handle 211. The locking mechanism 260 may comprise a dampening spring function especially when the locking mechanism is incorporated with or attached to the handle 211. The dampening spring function is further described below in relation to FIG. 4. A separately applicable locking mechanism may comprise a bodily fixed fastening device, such as a strap to encompass a bodily part or limb. The bodily fixed fastening device suitably comprises means for the locking mechanism to positionally lock the guidewire in relation to the bodily fixed fastening device. The main purpose of the locking mechanism of the guidewire is to be able to need/require less manual assistance. This relieves personnel from this task enabling them to work in a safer and possibly quicker manner. The locking mechanism locks the position of the guidewire in relation to one or more of a handle, an introducer, a sheath, a catheter, a body part, or an entry point.

Figure 3:
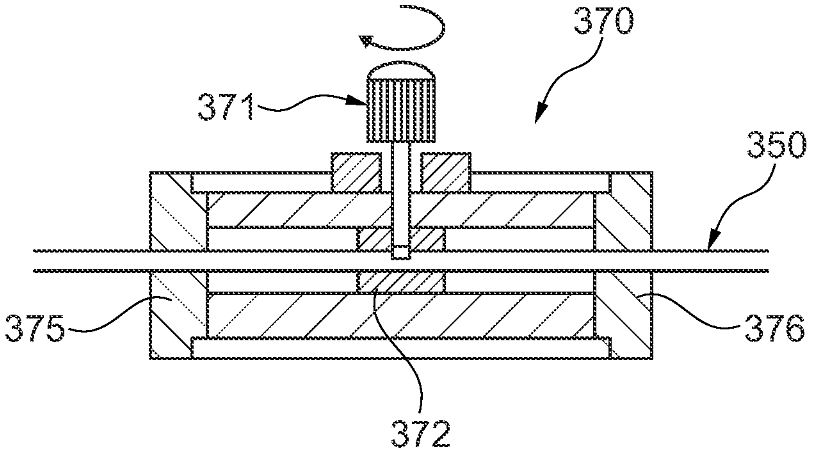
FIG. 3 illustrates schematically an example of a basic locking mechanism according to the invention.

FIG. 3 illustrates schematically an example of a basic locking mechanism 370 according to the invention. It comprises a clamping box 372 that is movably fixed in relation to a first end 375 and/or a second end 376 of the basic locking mechanism 370. A guidewire 350 to be positionally locked runs through the clamping box 372 and is positionally locked in relation to the clamping box 372 by means of a screw 371 that when screwed into the clamping box 372 will clamp a guidewire 350 to the clamping box 372. A guidewire 350 that is positionally locked to the clamping box 372 will be released and positionally unlocked by un-screwing the screw 371. The basic locking mechanism 370 may be an integral part of, permanently attached to or removably attached to a handle, for example such as previously described. If the locking mechanism is an integral part of a handle then the clamping box of the locking mechanism can be positionally/movably fixed in relation to a delivery system, a sheath, a catheter, a hypotube, or the handle itself. Alternatively, the basic locking mechanism 370 may be positionally attached to a body part, for example by means of a strap around a limb.

The clamping of a guidewire in a clamping box may be frictionally limited to allow a guide wire to move in relation to the clamping box if the guidewire is subjected to a force in relation to the clamping box that is above a first predetermined level. Alternatively, or additionally the locking mechanism may comprise a release mechanism, that releases a guidewire that is in a locked state into an unlocked state, when a guidewire is subjected to a force in relation to the clamping box that is above a second predetermined level. These additions are to prevent bodily harm from a distal end of a guidewire when a guidewire is in a locked state and the handle is moved intentionally or by accident.

Figure 4:
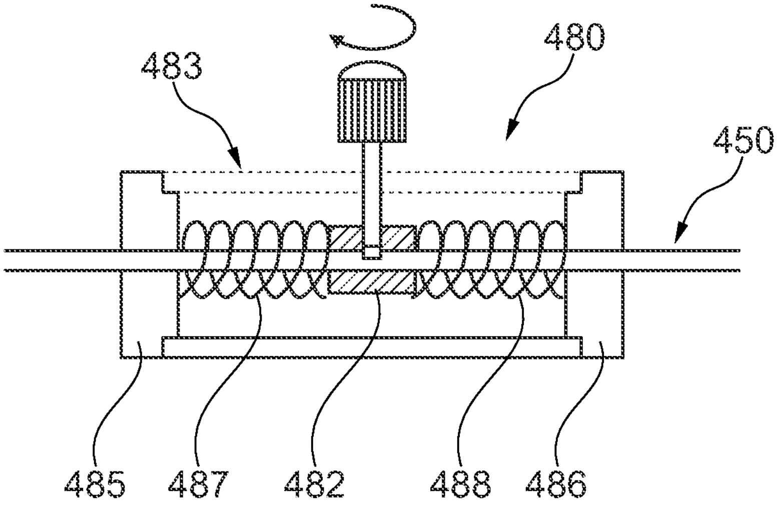
FIG. 4 illustrates schematically an example of a combined locking and dampening mechanism according to a further aspect of the invention.

FIG. 4 illustrates schematically an example of a combined locking and dampening mechanism 480 according to a further aspect of the invention. A dampening mechanism according to this illustrated embodiment is integrated with the locking mechanism. The dampening mechanism is to prevent bodily harm from a distal end of a guidewire when a guidewire is in a positionally locked state and the handle is moved intentionally or by accident.

Just like the locking mechanism according to FIG. 3, the dampening locking mechanism 480 according to FIG. 4 comprises a clamping box 482, a first end 485 and a second end 486. A guidewire 450 to be positionally locked running through the clamping box 482 and is positionally locked in relation to the clamping box 482 by means of a screw 471 that when screwed into the clamping box 482, the clamping box 482 will clamp a guidewire 450 to the clamping box 482. A guidewire 450 positionally locked to the clamping box 482 will be released and positionally unlocked by un-screwing the screw 471.

In contrast to the embodiment of FIG. 3, the clamping box 482 of the embodiment according to FIG. 4 is neither positionally locked in relation to the first end 485, nor in relation to the second end 486. The clamping box 482 is moveable between the two ends 485, 486 and a protective housing would then suitably have a slot 483 for the screw 471. In a preferred version of the embodiment, the movement of the clamping box 482 is dampened by at least one spring or spring function between the clamping box 482 and one of the ends 485, 486. Preferably there are two springs and/or spring functions, a first spring 487 between the clamping box 482 and the first end 485 and a second spring 488 between the clamping box 482 and the second end 486. The springs 487, 488 can be of a linear type or be of a progressive type. A linear spring has a spring rate that is consistent along the entire length of the spring as it is compressed. On the other hand, a progressive spring has a spring rate that increases or changes with the compression of the spring.

The two springs 487, 488 may be the same length and type, which would then position the clamping box 482 in the middle between the first end 485 and the second end 486 when in rest. This would result in a symmetrical dampening locking mechanism 480, which is suitable for a dampening mechanism 480 that is not integrated with a handle or does not comprise a connection element for attachment on only one correct/intended side, or for example keyed attachment connection elements. A symmetrical dampening locking mechanism cannot be turned in the wrong direction, working equally well in both directions. Preferably with an integrated or with a keyed attachment connection element to a handle, the dampening locking mechanism is asymmetrical having a longer stroke toward a proximal end of the dampening locking mechanism than a distal end towards a distal end of a guidewire. This is a safety mechanism to avoid the distal end of a guidewire being pushed into somewhere that could cause bodily harm.

In addition, as also described as an addition for the embodiment according to FIG. 3, the clamping of a guidewire 450 in a clamping box 482 may be frictionally limited to allow a guidewire to move in relation to the clamping box if the guidewire is subjected to a force in relation to the clamping box above a first predetermined level. Alternatively, or additionally the locking mechanism may also comprise a release mechanism, that releases a guidewire that is in a locked state into an unlocked state, when a guidewire in relation to the clamping box is subjected to a force above a second predetermined level. These additions are to further prevent bodily harm from the distal end of a guidewire when a clamping box 482 has by displacement reached one of the two ends 485, 486.

Figure 5:
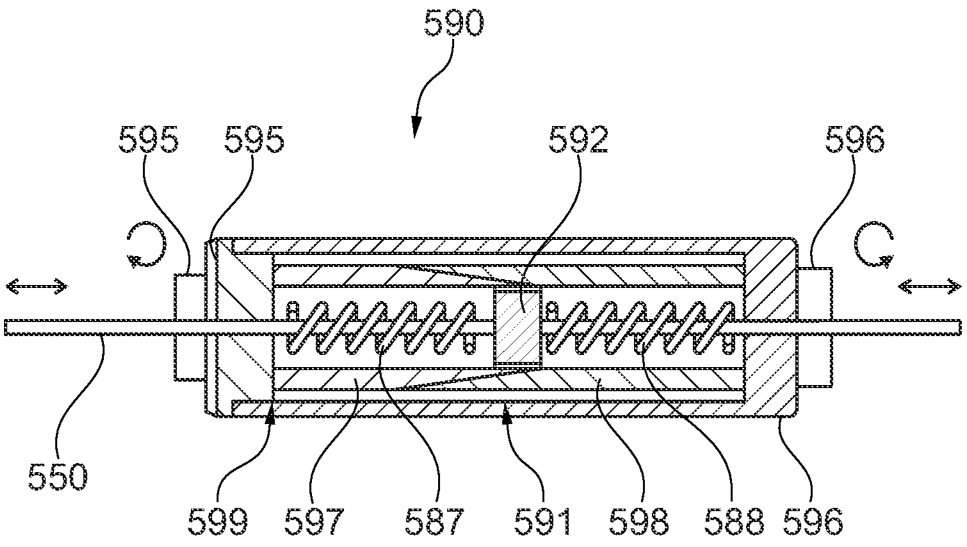
FIG. 5 illustrates schematically an example of a combined locking and dampening mechanism with a controllable release 490 according to a further aspect of the invention.

FIG. 5 illustrates schematically an example of a combined locking and dampening mechanism with a controllable release 590 according to a further aspect of the invention. The locking mechanism 590 comprises a first end 595 and a second end 596, a lock unit 592 therebetween with a spring 587, 588 on either side. The locking mechanism 590 according to the example is configured for a guidewire 550 to run between the two ends, through the two springs, and through the lock unit. Initially the lock unit will be located centrally in between the two springs, assuming that the two springs have the same length and the same spring characteristics. As the two ends are turned such that they come closer together, first a guidewire through the lock unit becomes positionally locked to the lock unit and then the lock unit will also become positionally locked within the locking mechanism with an increasing friction as long as the two ends are continued to be turned to move the two ends closer together. A force on the guidewire in relation to the locking mechanism that overcomes the friction will move the lock unit out of the locking region and releasing both the lock unit and the guidewire. Suitably the maximum friction attainable is such that a force on the guidewire in relation to the locking mechanism required to release the guidewire is less than a force that can cause damage by the guidewire. Turning the two ends in the opposite direction in relation to each other will then first decrease the friction with which the lock unit is positionally locked within the locking mechanism until both the lock unit and a guidewire through it will become positionally unlocked.

In the illustrated example the second end 596 comprises a tubular external extension 591 that reaches the first end 595 where the first end 595 and the extension 591 are attached with threads. By turning the first end 595 and the second end 596 in relation to each other, the first end 595 and the second end 595 will either move apart or move closer together depending on the threads and how the ends 595, 596 are turned in relation to each other. Internally the first end 595 is coupled to a first tubular extension 597 with a distal end that is externally tapered, and the second end 596 is coupled to a second tubular extension 598 with a distal end that is internally tapered. The tapered end of the first extension is inside the tapered end of the second extension, and at this place inside the first extension is where the lock unit is located. When the ends are turned such that the two ends come closer together then the lock unit becomes more and more squeezed positionally locking the guidewire to the lock unit. At the same time the friction also increases between the lock unit and the inside of the distal end of the first tubular extension. This increases a necessary force on the guide wire in relation to the locking mechanism before the lock unit will move. Once the lock unit moves out of the squeezed region, the guidewire becomes positionally unlocked from the lock unit.

To improve the function of the embolic protection device even further, a filter cleaning mechanism can be incorporated in cooperation with the filter. A particle might stick to the filter or get stuck in a crease of the embolic protection device. These potential sticky or stuck particle(s) might become dislodged during removal of the embolic protection device and flow somewhere unwanted. The cleaning mechanism may comprise one or more of:

A scraper attached to an optional (guide-) wire that is dragged and possible pushed back and forth over the filter of the embolic protection device.

A mechanical vibration of the hypotube attached to the embolic protection device and or to a guidewire within the hypotube. Ultrasonic and or vibration waves sent along the hypotube and/or a guidewire within the hypotube. There can alternatively be external ultrasonic or vibration stimulus. Can also be lower or higher frequencies.

A shaking mechanism of the guidewire.

To improve this cleaning mechanism even further, it is beneficial if the cleaning mechanism function is synchronized with the heartbeat, for example by means of EKG. Suitably the function is initiated at the beginning of the ventricular ejection and stopped before the ventricular ejection ends (ventricular systole, second phase). This to ensure that any particles that are dislodged by the cleaning mechanism are transported away from the area of the embolic protection device.

To improve the function of the embolic protection device still further, an embolic protection device removal synchronizer function can be incorporated in cooperation with the embolic protection device. As mentioned above, a particle might stick to the filter or get stuck in a crease of the embolic protection device. These potential sticky or stuck particle(s) might dislodge during removal of the embolic protection device and flow somewhere unwanted. The embolic protection device removal synchronizer function synchronizes the removal of the embolic protection device with the heartbeat, suitably by means of EKG or other suitable means. The removal of the embolic protection device should suitably be done during the interval when the blood pressure starts to increase since anything that is then dislodged will be flushed downstream. Otherwise, dislodged particles might just instead float about when the embolic protection device is folded and pulled away and then be flow up the previously filtered entrances when the pressure returns. A removal of an embolic protection device from its place of protection might thus take several heartbeats to complete.

The invention is based on the basic inventive idea of keeping an embolic protection device safely in place without less continuous manual intervention. The invention is not restricted to the above-described embodiments, but may be varied within the scope of the appended claims.

Some additional or alternative examples include:

1. An embolic protection assembly (201) comprising:

an embolic protection device (240), a sheath (220);

a tube (230) attached to the embolic protection device, wherein the assembly is configured for a guidewire (250, 350, 450, 550) to be drawn through the tube and the tube to be drawn through the sheath, wherein the assembly further comprises:

a locking mechanism (370, 480, 590), wherein the locking mechanism is configured in the assembly such that a guidewire drawn through the tube is also drawn through the locking mechanism, wherein the locking mechanism is in a first state configured to positionally lock a guidewire that is drawn through the locking mechanism and in a second state the locking mechanism is configured to allow a guidewire to positionally move.

2. The embolic protection assembly according to example 1, wherein the locking mechanism comprises a lock unit (372, 382) and wherein a guidewire is positionally locked in relation to the lock unit.

3. The embolic protection assembly according to example 2, wherein that the lock unit (372, 382) is configured to clamp a guidewire in the first state.

4. The embolic protection assembly according to example 2 or 3, wherein the locking mechanism (480, 590) further comprises a dampening function.

5. The embolic protection assembly according to example 4, wherein the dampening function comprises one or more springs and/or one or more spring mechanisms.

6. The embolic protection assembly according to example 5, wherein the one or more springs and/or one or more spring mechanisms are linear.

7. The embolic protection assembly according to example 5, wherein the one or more springs and/or one or more spring mechanisms are progressive.

8. The embolic protection assembly according to any one of examples 4 to 7, wherein the dampening function is symmetrical in relation to the lock unit.

9. The embolic protection assembly according to any one of examples 4 to 7, wherein the dampening function is asymmetrical in relation to the lock unit.

10. The embolic protection assembly according to any one of example 4 to example 9, wherein when the locking mechanism is in the first state the dampening function is configured to enable to displace the lock unit in relation to a first end of the locking mechanism up to a predetermined maximum length when a guidewire that is positionally locked is subjected to at least a third predetermined force level in relation to the locking mechanism.

11. The embolic protection assembly according to example 10, wherein the third predetermined force level is a function of the displacement of the lock unit.

12. The embolic protection assembly according to any preceding example, wherein the locking mechanism is further configured in the first state to subject a guidewire to a predetermined friction so that as long as a guidewire is subjected to a force in relation to the locking mechanism that is below a first predetermined force level, it is positionally locked.

13. The embolic protection assembly according to any preceding example, wherein the locking mechanism is further configured in the first state to change to the second state if a guidewire is subjected to a force in relation to the locking mechanism that is above a second predetermined force level.

14. The embolic protection assembly according to any preceding example, wherein the embolic protection device (240) comprises a filter (242) or a deflector unit (242).

15. The embolic protection assembly according to any preceding example, wherein the tube is directly or indirectly attached to the embolic protection device.

16. The embolic protection assembly according to any previous example, wherein the assembly further comprises a handle.

FIG. 1 illustrates an embolic protection assembly laid out flat in a deployed state.

100 An embolic protection assembly
110 A handle
112 A distal part of the handle
114 A proximal part of the handle
116 A guidewire port at a proximal end of the proximal part of the handle
120 A delivery system
130 A hypotube/a hypotube shaft/a tube
132 An atraumatic tip at a distal end of the hypotube
140 An embolic protection device
142 A deflection-filter of the embolic protection device
144 A device-tail/connection mechanism of the embolic protection device
146 A connector of the embolic protection device
150 A guidewire FIGS. 2*a* and 2*b* illustrate deployed embolic protection assemblies according to the invention in use.

201 An embolic protection assembly according to the invention
211 A handle
220 A delivery system
223 Forced arching of delivery system
230 A hypotube/a hypotube shaft/a tube
232 An atraumatic tip at a distal end of the hypotube
240 An embolic protection device
242 A deflection-filter
244 A device-tail/connection mechanism
250 A guidewire
251 Distal end of a guidewire formed as a pigtail
255 Valve
260 A locking mechanism FIG. 3 illustrates schematically an example of a basic locking mechanism

370 according to the invention.
350 A guidewire
370 A basic locking mechanism according to the invention
371 A screw
372 A fixed lock unit, clamping box/lockable passage
375 A first end of the locking mechanism
376 A second end of the locking mechanism FIG. 4 illustrates schematically an example of a combined locking and dampening mechanism 480 according to a further aspect of the invention.

450 A guidewire
471 A screw
480 A dampening locking mechanism according to the invention
482 A non-fixed lock unit, clamping box/lockable passage
483 A long narrow hole, a slot/slit for the screw to slide in
485 A first end of the locking mechanism
486 A second end of the locking mechanism
487 A first spring or spring function, linear or progressive
488 A second spring or spring function, linear or progressive FIG. 5 illustrates schematically an example of a combined locking and dampening mechanism with a controllable release 590 according to a further aspect of the invention.

550 A guidewire
587 A first spring or spring function, linear or progressive
588 A second spring or spring function, linear or progressive
590 A releasable dampening locking mechanism according to the invention
591 External, suitably tubular, extension of the second end 596
592 A non-fixed lock unit, clamping box/lockable passage
595 A first end of the locking mechanism
596 A second end of the locking mechanism
597 Internal tubular tapered extension of the first end 595
598 Internal tubular tapered extension of the second end 596
599 Threads between the first end 595 and the extension 591 of the second end 596

The invention claimed is:

1. An introducer assembly for minimally invasive deployment in a vessel, the introducer assembly comprising: a guidewire; a handle with a locking mechanism for locking the guidewire relative to said handle;

a medical device; and a delivery system, wherein the locking mechanism comprises a lock unit and wherein the guidewire is positionally locked in relation to the lock unit, wherein the locking mechanism further comprises a dampening function wherein the dampening function is symmetrical in relation to the lock unit.

2. The introducer assembly according to claim 1, wherein said medical device is an embolic protection device.

3. The introducer assembly according to claim 2, wherein said embolic protection device comprises a filter, a deflector unit, or a deflection filter.

4. The introducer assembly according to claim 3, wherein a tube is directly or indirectly attached to the embolic protection device.

5. The introducer assembly according to claim 2, wherein, in use in said vessel, a pressure on said embolic protection device by a tube is controllable by a position of said guidewire relative said handle to control a position of said embolic protection device in said vessel.

6. The introducer assembly according to claim 1, comprising a tube with a lumen for receiving said guidewire.

7. The introducer assembly according to claim 1, wherein said locking mechanism includes at least one spring arranged to provide limited relative movement of the guidewire relative the handle while in a locked state of the locking mechanism.

8. The introducer assembly according to claim 1, further comprising:

a tube attached to the handle, wherein the assembly is configured for the guidewire to be drawn through the tube, wherein the locking mechanism, is configured in the assembly such that the guidewire drawn through the tube is also drawn through the locking mechanism, wherein the locking mechanism is in a first state configured to positionally lock the guidewire that is drawn through the locking mechanism and in a second state the locking mechanism is configured to allow the guidewire to positionally move.

9. The introducer assembly according to claim 8, wherein the locking mechanism is further configured in the first state to change to the second state if the guidewire is subjected to a force in relation to the locking mechanism that is above a predetermined force level.

10. The introducer assembly according to claim 1, wherein the lock unit is configured to clamp the guidewire in a first state.

11. The introducer assembly according to claim 1, wherein the dampening function comprises one or more springs and/or one or more spring mechanisms, wherein the one or more springs and/or one or more spring mechanisms are linear or progressive.

12. The introducer assembly according to claim 11 wherein, when the locking mechanism is in a first state, the dampening function is configured to enable to displace the lock unit in relation to a first end of the locking mechanism up to a predetermined maximum length when the guidewire that is positionally locked is subjected to at least a predetermined force level in relation to the locking mechanism.

13. The introducer assembly according to claim 12, wherein the predetermined force level is a function of the displacement of the lock unit.

14. The introducer assembly according to claim 11, wherein the locking mechanism is further configured in a first state to subject the guidewire to a predetermined friction so that as long as the guidewire is subjected to a force in relation to the locking mechanism that is below a first predetermined force level, it is positionally locked.

* * * * *